United States Patent [19]

Sadler et al.

[11] Patent Number: 5,401,491

[45] Date of Patent: Mar. 28, 1995

[54] NMR CONTRAST AGENTS

[75] Inventors: John P. Sadler, Harrow Weald; Charles T. Harding, Bovingdon, both of England

[73] Assignee: Guerbet S.A., France

[21] Appl. No.: 912,581

[22] Filed: Jul. 13, 1992

Related U.S. Application Data

[63] Continuation of Ser. No. 440,433, Nov. 28, 1989, abandoned, which is a continuation of Ser. No. 827,963, Jan. 30, 1986, abandoned.

[30] Foreign Application Priority Data

May 31, 1985 [GB] United Kingdom ............ 8413849

[51] Int. Cl.$^6$ ............ A61K 49/00; A61K 31/715; A61K 31/19
[52] U.S. Cl. ............ 424/9; 514/53; 514/57; 514/59; 514/557
[58] Field of Search ............ 424/9; 128/653, 654; 436/173, 806; 514/57, 59, 53, 557, 60

[56] References Cited

U.S. PATENT DOCUMENTS

| | | | |
|---|---|---|---|
| 4,385,046 | 5/1983 | Milbrath et al. | 424/1 |
| 4,423,158 | 1/1983 | Porath | 521/32 |
| 4,615,879 | 10/1986 | Runge et al. | 424/9 |
| 4,647,447 | 3/1987 | Gries et al. | 424/9 |
| 4,719,098 | 1/1988 | Weinmann et al. | 436/806 |

*Primary Examiner*—Raymond Henley, III
*Assistant Examiner*—K. Weddington
*Attorney, Agent, or Firm*—Wenderoth, Lind & Ponack

[57] ABSTRACT

An agent for modifying $H_2O$ relaxation times in NMR diagnosis comprises a polysaccharide having chemically linked to it an organic complexant to which is complexed a paramagnetic metal ion. Polysaccharides include cellulose, starch, sepharose and dextran. Organic complexants include EDTA, DTPA and aminoethyl diphosphonate. A preferred metal ion is Gadolinium (III). The agents can be administered orally or parenterally.

19 Claims, No Drawings

NMR CONTRAST AGENTS

This application is a continuation of application Ser. No. 07/440,433, filed on Nov. 28, 1989, now abandoned, which is a continuation of now abandoned, Ser. No. 06/827,963, filed Jan. 30, 1986.

This invention relates to NMR (nuclear magnetic resonance) contrast agents, that is to say, to agents for modifying relaxation times, particularly proton relaxation times in NMR diagnosis. The agents of this invention are mostly suitable for administration to humans or other animals prior to NMR imaging in vivo.

German Patent Application 3129906 describes compounds for modifying relaxation times in NMR diagnosis comprising complexes of open-chain or cyclic complex formers with paramagnetic metal ions. For human NMR diagnosis, aqueous solutions of the complexes are administered orally, neurally or intravasally, and are said to be less toxic than simple inorganic salts of the paramagnetic metals.

However, the German Patent Application leaves several problems unsolved. Toxicity of the complexes is likely to be a problem, more particularly, where the complex is metabolisable. The biodistribution of the complex depends largely on the nature of the complex former, but this feature is not discussed. An NMR contrast agent is rather unlikely to be useful unless its transport and biodistribution are known and controlled with some accuracy. It is an object of this invention to overcome these problems.

The invention provides an agent for modifying relaxation times in NMR diagnosis comprising a polysaccharide having chemically linked to it an organic complexant to which is complexed a paramagnetic metal ion.

A possible advantage of the agents of this invention over simple complexes of paramagnetic metal ions is their greater influence on proton relaxation times which gives rise to better images for equivalent amounts of metal ion.

Various different polysaccharides, including chemical derivatives thereof, may be used, and will have an important influence on the properties of the agent. The polysaccharide may be water-soluble, such as dextran or dextrin, or water-insoluble, such as cellulose or SEPHAROSE or starch. SEPHAROSE is a bead-formed gel prepared by cross-linking agarose. Agents based on water-soluble polysaccharides may be administered orally or parenterally; agents based on water-insoluble polysaccharides are mainly suitable for oral administration.

The polysaccharide may be metabolisable or non-metabolisable by the animal to which it is administered. Compounds which are not metabolised within the time span required for NMR scanning are regarded herein as non-metabolisable, even though they may be metabolised over a much longer time span. Cellulose, Sepharose ® (an agarose-based gel marketed by Pharmacia, Uppsala, Sweden) and dextran are non-metabolisable by humans, whereas starch and dextrin are metabolisable. An advantage of using a metal ion complex bound to an insoluble non-metabolisable (by humans) polysaccharide is that orally administered agent should be confined to the gastro-intestinal tract and rapidly excreted in the faeces. This is important particularly when, as is often the case, the free paramagnetic metal ion would be toxic.

Suitable paramagnetic metal ions are well known in the field and include those of the lanthanide elements with atomic numbers 58 to 70 and those of the transition metals with atomic numbers 21 to 29, 42 and 44. Preferred are Mn(II), Cu(II), Fe(II), Gd(III), Fe(III), Cr(III), Dy(III) and V(IV). Factors affecting the choice of metal ion are its paramagnetic properties, the stability of the metal ion-complexant-polysaccharide moiety, its toxicity, and the extent to which the metal ion in the complex interacts with water so as to vary the proton relaxation times.

The organic complexing agent should preferably form a complex with the paramagnetic metal ion that is stable in vivo, and this is particularly important when the free metal ion would be toxic. The complexing agent may be one which forms a chelate with the chosen metal ion. Preferred are the aminopolyacetic acids such as Nitrilotriacetic acid
N,N,N',N'-ethylenediamine tetraacetic acid (EDTA)
N-hydroxyethyl N,N',N'-ethylenediamine triacetic acid
N,N,N',N'',N''-diethylene triamine pentaacetic acid (DTPA)
N-hydroxyethylimino diacetic acid.

Particularly preferred are EDTA and DTPA.

Other complexing agents include those having free amino groups, such as for example aminoethyl diphosphonate (AEDP) glutamic acid and δ-N-acyl-δ-N-hydroxyornithine.

The complexant may be chemically linked to the polysaccharide by known chemical methods for example by the use of cyanogen bromide. The possibility arises that a complexant directly linked to polysaccharide may be sterically hindered from chelating the paramagnetic metal ion. This risk may be avoided by the use of a linker molecule between the complexant and the polysaccharide. The chemistry may be represented thus:

where X is the polysaccharide residue, and n is up to 10, for example from 4–8. Then:

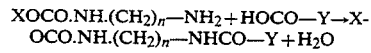

where Y is the complexant residue. The value of n is not critical. Indeed that the linker arm may not be needed at all in some cases. Where no linker is used, the complexant may be joined directly to the polysaccharide by known chemical techniques.

Various alternatives to cyanogen bromide are known for use to activate polysaccharides for reaction with amine-group-container linker arms (or direct with complexants). These include:

1) 1-cyano-4-dimethylamino pyridinium tetrafluoroborate-Cyanylating agent for covalent attachment of ligands to polysaccharide resins. Febs. Letts. Vol.154 No. 1 (1983) p.209.

2) Benzoquininone. BBA 386 (1975) 196–202.

3) Carboxymethyldextran. J. Applied Biochem. 2, 25–35 (1980)
4) Bisepoxirane. J. Chromatography 209, (1981) 363.
5) Divinylsulphone Meth. Enzymology 34, (1974), 27.
6) Epichlorohydrin J. Chromat. 51 (1970) 479. J. Immunol. Meth. 58 (1983) 93–107.
7) Carbonyldiimidazole J. Chromatography, 196, (1980) 379.
8) Periodate Immunology 20, (1974) 1061.
9) Cyanuric chloride Anal. Biochem. 87 (1978) 77. U.S. Pat. No. 3,956,272 Affinity Chromatography, Elsevier Scient. Publ. Co. 1978. p.34–44 p.154, p.324–326.
10) Tosyl chloride B. B. Res. Comm. 102 (1981) 449 Eur. J. Biochem. 112 (1980) 397
11) p-Nitro benzyl chloride.
12) 2-Aminoethyl hydrogen sulphate (dextran amine) E. Jellum. Biochem. Pharm., 22, 1179 (1973). It is generally convenient to form the chelate with the paramagnetic ion as the final stage of the reaction sequence. This may be done simply by mixing an aqueous solution of the paramagnetic metal ion with the polysaccharide-complexant and allowing the mixture to stand, preferably with prior neutralization of some or all of the protonated metal binding sites of the complexant.

When the polysaccharide is insoluble, its physical state will depend on how it is to be administered. Finely divided material is preferably used; for example, 5 micron fibrous cellulosic material. This increases the specific surface area, and hence may increase the rate and extent of reaction with the complexant. It is this reaction that determines how much paramagnetic metal ion can be attached to unit weight of polysaccharide. Useful NMR contrast agents should contain at least one paramagnetic metal ion per 200 sugar units, perferably at least one per 100 sugar units, of the polysaccharide.

The agents may be administered orally, e.g. to visualise the gastro-intestinal tract; or parenterally e.g. to act as blood pool agents.

The following examples illustrate the invention. Examples 1 and 3 to 6 show preparation of various NMR contrast agents according to the invention. Examples 2 and 7 to 10 demonstrate properties of some of these agents in vivo and in vitro.

EXAMPLE 1

Gd(III) Cellulose-linker-DTPA (GdcDTPA)

i) Synthesis ii) Gd(III) binding i) Synthesis (a) DTPA →DTPA ANHYDRIDE 40 g DTPA and acetic acid anhydride (38 ml) in pyridine (50 ml) for 24 hours at 55° C. (oil bath). DTPA anhydride then purified by filtration, washed with acetic anhydride (100 ml) and anhydrous ether (200 ml). Dried in an oven at 50° C. overnight. IR spectrum recorded (b) ACTIVATION OF CELLULOSE Cellulose (20 g) and CNBr (10 g in DMSO) mixed in NaOH solution pH 10.7 (100 mls), pH falls rapidly, brought up to pH 10.7 with 2M NaOH addition. Mixture stirred for 25 minutes (if stirred longer then crosslinking may occur between the sugar units).
IR spectrum of activated cellulose recorded.

(c) ACTIVATED CELLULOSE+LINKER→CELLULOSE-LINKER

Activated cellulose (20 g)+linker (25 g) [1,4-diaminobutane; 1,6-diaminohexane; 1,8-diaminooctane] in 300 mls $H_2O$ and stirred for 3 hours at room temperature, maintained at pH 7 by HCl additions. Insoluble product recovered and dried.
IR spectrum of cellulose-linker recorded.

(d) CELLULOSE-LINKER+DTPA ANHYDRIDE→cDTPA 2 methods:

1st method (higher yield of cDTPA—see later)
  20 g cellulose-linker suspended in redistilled DMF (200 ml), bis anhydride DTPA (10 g) added. Stirred for hours at 40° C. Product collected and washed (DMF 300 ml, $H_2O$ 200 ml).

2nd method
  20 g cellulose-linker suspended in $H_2O$ (200 ml), bis anhydride (10 g) added. Stirred for 24 hours at room temperature. Product collected and washed ($H_2O$ 2000 ml).

Summary
Four cDTPA polymers have been produced:
KEY:
  $c_4$DTPA cellulose-butane linker-DTPA: DMF last stage
  $c_8$DTPA cellulose-octane linker-DTPA: DMF last stage
  $c_6$DTPA cellulose-hexane linker-DTPA: DMF last stage
  $c_6$DTPA (aq) cellulose-hexane linker-DTPA: $H_2O$ last stage ii) Binding of Gd(III) to $c_n$ DTPA (where n = 4, 6 or 8)  (1) Gd(III) binding to $c_n$DTPA
                       (2) $T_1$ and $T_2$ relaxation times (1) Gd(III) binding to $c_n$DTPA 0.5 g $c_n$DTPA + $5 \times 10^{-5}$ mols Gd(III) ions (10 mls of $5 \times 10^{-3}$M Gd(NO$_3$)$_3$.5H$_2$O. Sample shaken for 1 hour and then spun down (4000 rpm for 3 minutes); linewidth of aqueous layer recorded at 60 MHz (room temperature).

| Tube | Sample | | Line Width (Hz) | Gd (III) Bound/mol |
|---|---|---|---|---|
| 1 | | 5 mM Gd (III) | 25 | 0 |
| 2 | 0.5 g | $c_6$ DTPA + 5 mM Gd (III) | 7 | $4.5 \times 10^{-5}$ |
| 3 | 0.5 g | $c_6$ DTPA (aq) + 5 mM Gd (III) | 14 | $2.9 \times 10^{-5}$ |
| 4 | 0.5 g | $c_4$ DTPA + 5 mM Gd (III) | 5 | $4.6 \times 10^{-5}$ |
| 5 | 0.5 g | $c_8$ DTPA + 5 mM Gd (III) | 5 | $4.6 \times 10^{-5}$ |

Results imply that a higher uptake of Gd(III) occurs when DMF media are used in the final stages of $c_n$DTPA synthesis and the length of linker does not influence the number of Gd(III) ions that bind.

Gd binding was confirmed by ESR, electron spin resonance, and EM, electron microscopic x-ray analysis.

(2) Influence of $c_6$DTPA and $Gdc_6$DTPA on the $T_1$ and $T_2$ relaxation times of water 10 mm NMR tube, 2 ml $H_2O/D_2O$ (70:30) added. $T_1$ measured at 200 MHz at room temperature using the inversion-recovery pulse sequence. 0.25 g cDTPA added. Tube shaken and $T_1$ recorded. 2 ml Gd(III) ions ($5 \times 10^{-3}$M $Gd(NO_3)_3.5H_2O$ i.e. $10^{-5}$ mol Gd(III) ions) added. Left shaking for 1 hour, sample washed and 2 mls $H_2O/D_{20}$ added. $T_1$ measured under the same previous conditions.

| Sample (2 ml) | $T_1$/s at 200 MHz |
|---|---|
| (1) $H_2O/D_2O$ | 3.74 |
| (2) $H_2O/D_2O$ + 0.25 g cDTPA | 3.23 |
| (3) $H_2O/D_2O$ + 0.25 g GdcDTPA | 1.30 |

0.017 g $Gdc_6$DTPA evenly suspended in 0.7 mls $H_2O/D_2O$ (70:30) in 5 mm NMR tube. Line width recorded at 60 MHz for a non-spinning sample (if spinning then a centrifugal force acts on the $Gdc_6$DTPA causing the complex to settle faster).

A line-width of 34 Hz was observed compared to 7 Hz for a similar sample of $H_2O/D_2O$ alone, showing that 0.017 g of $Gdc_6$DTPA decreased the $T_2$ of water by a factor of about five.

Summary 0.5 g $c_n$DTPA bind approximately $5 \times 10^{-5}$ mol Gd(III)ions. 0.25 g $Gdc_6$DTPA decreases the $T_1$ value $H_2O$ by a factor of 2.88 and decreases the $T_2$ value of $H_2O$ by a factor of ca.5. NMR studies showed that the length of linker did not influence the number of mol Gd(III) ions that bound. Calculation showed that one linker molecule attaches to every 65 sugar units of the cellulose.

EXAMPLE 2

AIM

To follow $^{153}$Gd(III) uptake by $c_6$DTPA, and study $^{153}$Gdc$_6$DTPA passage through four rat gastrointestinal tracts.

PROCEDURE 0.5 g $c_6$DTPA soaked overnight in Tris buffer (pH 7.2). Washed via centrifugation with $3 \times 10$ ml portions saline. 1.5 ml $^{153}$GdCl$_3$/HCl in 5 ml acetate buffer(pH 5.6), counted, activity determined, then added to $c_6$DTPA and left on roller for 2 hours. Solution spun down and number of counts in aqueous layer determined (therefore deduce % uptake of $^{153}$Gd(III) by $c_6$DTPA).

$0.32 \times 10^{-4}$ mol $Gd(NO_3)_3.5H_2O$ added to mixture, left on roller for 1 week, spun down and number of counts in aqueous medium determined. After 2 hours post innoculation of 0.5 g $c_6$DTPA with 1.5 ml $^{153}$GDCl$_3$ there was 91.5% incorporation of $^{153}$Gd onto $c_6$DTPA.

After 1 week post innoculation there was 63.2% incorporation of $^{153}$Gd onto DTPA.

The decrease can be attributed to dissociation of $^{153}$Gd(III) after cold Gd(III) ion addition.

After washing there was only a 0.92% loss of $^{153}$Gd, implying that the $^{153}$GdcDTPA was stable.

The $^{153}$Gdc$_6$DTPA then resuspended in 5 mls $H_2O$ (0.06 mCi/ml). 1 ml then administered to 4 Sprague Dawley male rats (already acclimatised in metabolism cages 3 days before dosing). Each rat anaesthetised lightly with ether before oral administration (1 ml of complex via a 200 mm long portex 6 FG catheter). After dosing count rates were taken in a twin NaI crystal counter, together with a dosing standard. Urine and faeces collected 5 hours, 24 hours and 48 hours after dosing, 2 rats dissected at 24 hours, other 2 dissected at 48 hours. The organs, urine and faeces were assayed for $^{153}$Gd in an autogammacounter.

RESULTS AND DISCUSSION (1) By 24 hours post dosing 97% of $^{153}$Gd(III) had been excreted in the faeces, implying no degradation of $^{153}$Gdc$_6$DTPA to soluble products which would then be excreted in the urine.

(2) After 48 hours post dosing approximately 100% of $^{153}$Gd(III) had been excreted (via faeces). Urine figures of 0.3% and 0.7% could be slight faecal contamination.

(3) The 0.4% blood figure represents a less than twice background rate.

(4) No accumulation of $^{153}$Gd(III) occurred in the organs assayed outside the GI tract at 24 or 48 hours post dosing.

| ANIMAL ORGAN | 22 hrs sacrifice | | 46 hrs sacrifice | | mean |
|---|---|---|---|---|---|
| | rat 1 | rat 2 | rat 3 | rat 4 | |
| Stomach | | 1.2% | | | |
| Small intestine | | 0.5% | | | |
| Large intestine | 0.2% | 2.8% | | | |
| Bladder/urine | | 0.3% | | 0.7% | |
| Blood | | | | 0.4% | |
| Faeces 22 hrs. | 99.8% | 95.2% | 98.2% | 94.9% | 97% |
| Faeces 48 hrs. | | | 1.8% | 3.9% | |
| Bone and other organs | 0% | 0% | 0% | 0% | |

Summary $^{153}$Gd(III) labelling of $c_6$DTPA was approximately 60% efficient (however cold Gd(III) present in excess).

On administration into rats, via oral route, 97% of $^{153}$Gdc$_6$DTPA was excreted from the body in the faeces, implying no Gdc$_6$DTPA retention, and stability of the complex to the GI tract.

The radioactive work on $^{153}$Gdc$_6$DTPA and the data collected on Gdc$_n$DTPA relaxation properties indicates that Gdc$_n$DTPA is a potential oral contrast agent.

EXAMPLE 3

Gd(III) Starch Linker DTPA (GdStDTPA)

Another water-insoluble agent was prepared by the method described in Example 1 but using starch as the starting polysaccharide in place of cellulose, and has been designated GdStDTPA.

6 g starch in 300 ml $H_2O + 2$ ml 2M NaOH; pH of solution 10.5. Stirred for 5 minutes, 2.2 g CNBr (in 2 ml DMF) added dropwise, pH 10 maintained for 20 minutes by 2M NaOH addition. Then HCl added, pH lowered to 7. 3.2 g 1,6-diaminohexane added, pH 7 maintained by HCl addition for 3 hours (constant stirring at room temperature) then filtered and washed with 500 ml water. The product starch-linker then taken up in 250 ml DMF (at 55° C.). 2 g DTPA anhydride added, mixture stirred for 12 hours at 55° C.—then product starch-linker-DTPA (stDTPA) washed (300 ml DMF and 500 ml $H_2O$). Gd(III) ion binding was confirmed by electron spin resonance (ESR) analysis of a saturated GdStDTPA sample.

The $H_2O$ $T_1$ relaxation time for a Gd(III) saturated GdStDTPA derivative was shown to be 142.2 ms for a 0.12 g/ml—shorter than for GdcDTPA under the same conditions.

EXAMPLE 4

Gd(III) SEPHAROSE-linker-DTPA (GdsDTPA)

i) Synthesis ii) Gd(III) binding

1) Synthesis

CNBr-activated SEPHAROSE (1 g) swollen on a sintered glass funnel for 15 minutes with 1 mM HCl (10 ml), then washed with 1 mM HCl (200 ml/g SEPHAROSE), the HCl preserves the activity of the reactive groups which hydrolyse at high pH. The gel then washed with 5 ml coupling buffer (0.25M NaHCO$_3$+0.5M NaCl; pH 8.5–9.0).

The gel is transferred to a solution of buffer (30 ml) containing 1,6-diaminohexane (0.8 g) and mixed on a rotating wheel (30 r.p.m) for 2 hours at room temperature. Use of a magnetic stirrer at this stage will break up the agarose units and a low MWT product is formed. The product is then washed on a sintered funnel; buffer (20 ml) then DMF (20 ml). The last wash with DMF, is critical as the next stage must be anhydrous.

The washed gel then transferred to a flask containing DMF (50 ml) and DTPA anhydride (0.5 g in minimal volume of DMSO). Mixture stirred for a minimum of 6 hours, on a rotating wheel at room temperature. The gel then washed (via sintered funnel) with DMF (50 ml) then H$_2$O (100 ml). A solution of glutamic acid may then be administered (20 ml) as this blocks any extra groups that do not have linker attached.

ii) Gd(III) binding to sDTPA

Gd(III) binding can be demonstrated, by NMR, by following the change in line-widths of the water resonance peak.

1 g sDTPA placed on sintered glass funnel, 10 ml Gd(III) ions added (5×10$^{-3}$M Gd(NO$_3$)$_3$.5H$_2$O—known line-width). The mixture gently agitated for 1 hour. The supernatant washed through and collected, and subsequent line-width recorded. A decrease in line-width represents Gd(III) binding (i.e. the concentration of Gd(III) in the aqueous solution has decreased). H$_2$O (5 ml) added to the gel, and shaken gently for 1 hour. The supernatant washed through and the line-width recorded. The wash process repeated a second time. The line-width of 0.5 g GdsDTPA/0.7 mls H$_2$O recorded, to show Gd(III) binding had occurred.

All line widths recorded at 60 MHz.

Results

| Tube | Sample | Line Width (Hz) |
|---|---|---|
| 1 | H$_2$O | 4 |
| 2 | 5 × 10$^{-3}$ M Gd (III) | 30 |
| 3 | Supernatant | 6 |
| 4 | 5 ml Wash (1st) | 4 |
| 5 | 5 ml wash (2nd) | 4 |

0.5 g Gd sDTPA/0.7 mls H$_2$O gave a line-width of 140 Hz compared to 0.5 g sDTPA/0.7 ml H$_2$O which gave a line-width of 14 Hz. The T$_1$ was reduced to less than 10 ms for the Gd sDTPA polymer (0.5 g/0.7 ml H$_2$O) compared to 3000 ms for sDTPA at the same concentration.

Deductions

The decrease in line-width of the H$_2$O wash implies that 1 g sDTPA binds approximately 5×10$^{-5}$ mol Gd(III) ions.

On washing the gel twice, no increase in the water line-width of the wash was observed, hence the complex GdsDTPA is stable.

NMR analysis of acid hydrolysate of sepharose-linker units suggests that one linker is attached to every 70 sugar units in the sepharose.

EXAMPLE 5

Gd(III) Dextran-linker-(GddDTPA)

i) Synthesis ii) Paramagnetic metal ion binding i) Synthesis of dDTPA 2 g dextran (18,000 MW) in a round-bottomed flask+150 ml H$_2$O (at least 150 ml, otherwise cross-linking occurs and a white ppt. forms on CNBr activation). 1 g CNBr (minimal vol. DMSO) added, solution maintained at pH 10.7, by 2M NaOH addition, for 20 minutes. After 20 minutes, or when signs of cross-linking were observed (white precipitates forming), the next stage was conducted.

1,6-diaminohexane (1.2 g) added to solution mixture, which then was subsequently diluted to 300 mls and stirred for 3 hours (room temperature), pH maintained at pH 7.4.H$_2$O then removed by rotary evaporation, leaving an oily product (very viscous dextran solution). DMF (100 mls) added and DTPA anhydride (1 g in DMSO). Mixture stirred for 12 hours at room temperature, very gently, by magnetic stirrer.

DMF then extracted by rotary evaporation. The viscous solution then poured into a presoaked dialysis sack and dialysed over 24 hours (4×3 liter water changes). The product then poured into a round-bottom flask and freeze-dried overnight.

ii) Binding of Paramagnetic metal ions to dDTPA 18,000 MW)

(1) Four sample tubes prepared, each containing 10 ml H$_2$O and 2.23 mg MnSO$_4$.4H$_2$O (10$^{-3}$M). Increasing amounts of dDTPA added to successive tubes. Line widths recorded at 60 MHz. Results then tabulated. They indicate the binding of Mn(II) to dDTPA.

| Tube | dDTPA/g | Line Width (Hz) |
|---|---|---|
| 1 | 0 | 75.6 |
| 2 | 0.0054 | 65.6 |
| 3 | 0.054 | 8.4 |
| 4 | 0.09 | 7 |

NMR analysis of the hydrolysate suggests that one linker was attached to every 43 sugar residues of dextran.

Gadolinium binding to dDTPA polymers has been shown by ESR; having incubated a mixture of dDTPA (82,000 MW) Gd(NO$_3$)$_3$.5H$_2$O for half an hour and then dialysing the resultant solution for 24 hours, the ESR of the dialysed solution was recorded and showed GD(III) had been retained by binding to the polymer. H$_2$O T$_1$ measurement of the GddDTPA polymers has been recorded and compared to dextran aqueous solutions alone.

| Tube | [Gd (III)]/mM | dDTPAg/ml | T1 (200 MHz at 300° K.) |
|------|---------------|-----------|-------------------------|
| 1 | 0 | 0.125 | 3180 ms |
| 2 | 0.5 | 0 | 232 ms |
| 3 | 0.5 | 0.11 | 633 ms |
| 4 | 1 | 0 | 105 ms |
| 5 | 1 | 0.11 | 290 ms |
| 6 | 10 | 0 | 9 ms |
| 7 | 10 | 0.11 | 28 ms |

Results show that Gd(III) binds to dDTPA and that GddDTPA is an effective relaxation agent.

This experiment was repeated using starting dextran material of different molecular weights (9000, 18000, 82000, 110000 and 150000). This polymer type was also synthesised and characterized via carboxymethyl dextran (ref 3), tosyl chloride (ref 10), and dextran amine (ref 12).

EXAMPLE 6

Gd(III) Dextan Aminoethyldiphosphonate (GddAEDP)

Dextran (82,000 MW) was activated via chloroacetic acid to carboxymethyl dextran (Ref 3). The activated dextran (3 g) was taken up in 20 mls $H_2O$. An aqueous solution of aminoethyl dihydrogen phosphate (0.5 g) was added, with adjustment of solution to pH 5-8. After 10 minutes stirring, 0.6 g of 1-ethyl-3-(3 dimethylaminopropylcarbodiimide). HCl was added, (pH 5-8 maintained). The solution was stirred for one hour, and both additions were repeated twice. After the final addition, the mixture was stirred for 12 hours and the solution then dialysed (4×3 liter $H_2O$ charges over 24 hours). Gd(III) Metal uptake was shown by ESR analysis on a dialysed solution mixture of $Gd(NO_3)_3 \cdot 5H_2O$ and dAEDP.

EXAMPLE 7

Samples of $Gd^{153}dDTPA$ (18,000 MW) were administered orally to rabbits at dosages of 11-14 mg/kg body weight. The radioactivity was totally excreted in the faeces within 72 hours. Activity in the urine was negligible, indicating no breakdown or absorption of the complex.

EXAMPLE 8

Aqueous solutions of GddDTPA (18,000 MW)(4 mg/ml physiological saline) were administered to three male Sprague Dawley rats and to two rabbits at dosage levels of 10 mg/kg and 2.5 mg/kg respectively. No adverse effects were noted.

EXAMPLE 9

The contrast enhancement properties of $Gdc_6DTPA$ and GddDTPA in saline solution were demonstrated at 6.4 MHz by observing proton NMR images of an array of test tubes as phantoms.

EXAMPLE 10

To demonstrate contrast enhancement in vivo, a total of 100 mg of GddDTPA (18,000 MW) was administered orally in ca. 50 ml of physiological saline solution to a rabbit under anaethesia. During the next few hours proton NMR images at 6.4 MHz of cross-sections showing the stomach and bowel regions were recorded using progressive saturation and inversion recovery pulse sequences. Contrast appeared in selected regions of the image due to shortening of the proton relaxation times. For example, the fluid in the stomach became white in colour whereas previously it was black and indistinguishable from the gases in the space above it (black being indicative of a low proton density or long relaxation time of protons). Similarly loops of bowel were also now distinguishable.

We claim:

1. A method of NMR diagnosis comprising administering to a patient an effective amount for modifying relaxation time of a polysaccharide selected from the group consisting of dextrans, dextrins, starch, cellulose and agarose, having chemically linked to it an organic complexant to which is complexed a paramagnetic metal ion.

2. The method as claimed in claim 1, wherein the polysaccharide is selected from cellulose, starch or agarose.

3. The method as claimed in claim 1, wherein the polysaccharide is dextran.

4. The method as claimed in claim 3, wherein the dextran has a molecular weight from 9,000 to 15,000.

5. The method as claimed in claim 1, wherein the organic complexant is an aminopolyacetic acid.

6. The method as claimed in claim 5, wherein the organic complexant is DTPA.

7. The method as claimed in claim 5, wherein the organic complexant is EDTA.

8. The method as claimed in claim 5, wherein the organic complexant is N-hydroxyethylimino diacetic acid.

9. The method as claimed in claim 1, wherein the complexant is directly linked to the polysaccharide.

10. The method as claimed in claim 1, wherein the complexant is linked to the polysaccharide by means of the linker $NH_2-(CH_2)_n-NH_2$ in which n is up to 10.

11. The method as claimed in claim 10, wherein the polysaccharide has been activated for the reaction with said linker by means of a chemical compound selected from cyanogen bromide, chloroacetic acid, bisepoxirane, epichlorohydrin, carbonyldiimidazole, periodate and tosyl chloride.

12. The method as claimed in claim 1, wherein the polysaccharide has been activated for the linkage with said complexant by means of a chemical compound selected from cyanogen bromide, chloroacetic acid, bisepoxirane, epichlorohydrin, carbonyldiimidazole, periodate, tosyl chloride and 2-aminoethyl hydrogen sulfate.

13. The method as claimed in claim 1, wherein the paramagnetic metal ion is selected from the lanthanide elements with atomic numbers 58 to 70 and those of the transition metals with atomic numbers 21 to 29, 42 and 44.

14. The method as claimed in claim 1, wherein at least one paramagnetic metal ion is present per 100 sugar units of the polysaccharide.

15. The method as claimed in claim 1, wherein said polysaccharide is administered by the oral or parenteral route.

16. The method as claimed in claim 1, wherein the polysaccharide is a water soluble polysaccharide.

17. The method as claimed in claim 1, wherein the polysaccharide is a water insoluble polysaccharide.

18. The method as claimed in claim 3, wherein the dextran has a molecular weight of 18000 to 82000.

19. A method for visualizing the gastro-intestinal tract comprising administering by the oral route a polysaccharide selected from the group consisting of dextrans, dextrins, starch, cellulose and agarose having chemically linked to it an organic complexant to which is complexed a paramagnetic metal ion.

* * * * *